United States Patent [19]

Cabbiness

[11] 4,058,366
[45] Nov. 15, 1977

[54] DETERMINATION OF FLOW CHARACTERISTICS OF PETROLIFEROUS FORMATIONS

[75] Inventor: Dale K. Cabbiness, Ponca City, Okla.

[73] Assignee: Continental Oil Company, Ponca City, Okla.

[21] Appl. No.: 747,451

[22] Filed: Dec. 3, 1976

Related U.S. Application Data

[63] Continuation-in-part of Ser. No. 643,286, Feb. 6, 1976, abandoned.

[51] Int. Cl.² ............................................. G01N 33/24
[52] U.S. Cl. .............................. 23/230 EP; 23/230 R; 166/250
[58] Field of Search ............ 23/230 M, 230 B, 230 R, 23/230 EP

[56] References Cited

U.S. PATENT DOCUMENTS

| | | | |
|---|---|---|---|
| 3,112,182 | 11/1963 | Brown | 23/230 EP |
| 3,743,613 | 7/1973 | Coulter | 175/65 |
| 3,792,044 | 2/1974 | Dooley | 23/230 B |
| 3,847,548 | 11/1974 | Keller | 23/230 EP |
| 3,908,760 | 9/1975 | Clampitt | 175/65 |

OTHER PUBLICATIONS

C. A. Browne et al., Physical & Chemical Methods of Sugar Analysis, 3rd Edition, 856,865, John Wiley & Sons, New York, 1941.

*Primary Examiner*—Sidney Marantz
*Attorney, Agent, or Firm*—Cortlan R. Schupbach, Jr.

[57] ABSTRACT

A method for determining the flow characteristics of subterranean petroliferous formations by injecting a tracer and a polysaccharide polymer having glucose moieties into said formation, recovering said tracer and polysaccharide from production well effluent at timed intervals and determining flow characteristics by the rate differential observed of the concentration of each in the effluent. Accurate determination of polysaccharide polymer is obtained by hydrolyzing the polymer to release glucose, reacting the glucose with orthotoluidine and determining the polymer concentration using colorimetric techniques.

7 Claims, No Drawings

DETERMINATION OF FLOW CHARACTERISTICS OF PETROLIFEROUS FORMATIONS

This application is a continuation-in-part of Serial Number 643,286 filed February 6, 1976, now abandoned.

This invention relates to a method for determining the flow characteristics of subterranean formations by analyzing polysaccharide polymers recovered from production wells. More particularly, this invention relates to an improved method for determining flow characteristics of such polymers through petroliferous formations by hydrolyzing the polymer to separate glucose moieties contained therein and analyzing for the concentration of such moieties.

As available oil supplies in producing formations have been depleted, additional recovery techniques have been developed to further extract oil trapped in petroliferous formations. Among such tertiary recovery techniques is waterflooding, generally carried out by injecting water at an injection well and displacing oil from the formation toward a producing well. Often polymers and other ingredients are added to such waterflood solutions to thicken and stabilize the solution, thus controlling the viscosity of the waterflood and adjusting the viscosity to the particular formation under development. In such cases the polymer often acts as a "piston" as relates to the less viscous hydrocarbons and pushes them toward the production well.

It is important that the characteristics of the formation undergoing tertiary recovery techniques be determined. Methods commonly used for detecting formation structures such as acoustical techniques are insufficiently precise for determining the porosity and flow characteristics of a formation. This information is needed in order to adequately design the most efficient tertiary recovery techniques. Since tertiary recovery techniques are extremely expensive to implement, it is of great importance to determine the particular treatment which provides maximum recovery.

It is therefore an object of the present invention to provide a reliable method for determining flow characteristics in petroleum reservoir formations and other subterranean formations. Other objects will become apparent to those skilled in this art as the description proceeds.

It has now been discovered according to the present invention that injecting a tracer and a polysaccharide polymer containing glucose moieties into a injection well and passing these materials through a formation to a production well, recovering them from the production well effluent, and analyzing for concentrations of each the relative concentration of each over a period of time will giving precise relative flow characteristics for petroliferous formations.

Information concerning the effectiveness of such water flooding can be determined by analyzing polymer obtained from production well effluent. In the past, attempts to analyze the polymers obtained from production wells have been based on a resorcinol analytical procedure and have not been wholly satisfactory. Resorcinol analytical procedures are subject to interferences caused by other ingredients in the waterflooding material and by bactericides such as acrolein added to waterfloods. Acrolein is the chief agent in causing the interference, and is frequently added to the waterflood in order to prevent biodegradation of the polymer and prevent well plugging because of bacterial activity. The instant invention provides both a method for determining flow characteristics of subterranean formations and a reliable method of analyzing the glucose moieties of the polysaccharide polymer, without which the flow characteristics of the subterranean formation could not be determined as accurately.

Tracers and polysaccharide polymers, in the past, have been inserted through a common borehole in entirely separate injections, such that a zone of tracer followed polymer passed through the formation. Usually the two were separated by a buffer zone of a nonreactive material such as water or surfactant. In the instant invention, both are injected simultaneously.

It has long been known that subterranean formations containing hydrocarbons recoverable by tertiary recovery techniques are of widely varying characteristics. One of the most important characteristics which must be determined before mapping out a total tertiary recovery program is the flow characteristics and average porosity of said formations. In the past, tracer elements such as thiocyanate, bromide and radioactive ions, ethanol and methanol have been injected into the formation and recovered over a period of time from production wells at varying distances from the injection well. However, these tracers are normally materials of very small molecular weight which can easily find their way into all of the interstices of the formation and thus tend to come out of the formation in a production well effluent at relatively constant rates. It has now been determined that, when in addition to a tracer, a polysaccharide polymer is injected into the formation, relative speeds of passage through the formation can be adequately determined by measuring the concentration of both the tracer and the polysaccharide when taken at various points in time. Since the polysaccharide is a higher molecular weight material, it does not have access to all the interstices of the formation, and thus must take the path of least resistance, bypassing the small interstices.

As those skilled with chemical analytical procedures will appreciate, the result is much like that of a resin elution column in which the smaller materials pass through the pores of a resin and thus travel a greater distance than the higher molecular weight materials, resulting in their eluting from the column as the last material whereas the higher molecular weight materials are the first to be eluted. A comparison of the tracer material and the polysaccharide polymer will yield adequate and accurate information as to the flow and pore characteristics of a subterranean formation when compared to data taken from standard samples of known pore size.

Equal volume samples are obtained from the production well effluent, and a separate sample is tested for each tracer involved and a sample tested for polysaccharide polymer content. More than one tracer can be used, but all provide similar information.

Concentrations of tracer in the effluent sample are determined by methods well known to those skilled in this art. For example, thiocyanate and bromide concentrations are determined by colorimetric procedures, specific ion electrodes or x-ray methods. Radioactive ions require well-known radiation technique while alcohol tracers are determined by gas/liquid chromatography (GLC) methods also well-known to those skilled in this art.

An important feature of the instant invention is the method of analyzing the biopolysaccharide polymer content of the production well effluent. As previously described, the polymer must contain bactericides and other ingredients in order to prevent its degradation or plugging of the formation. However these very same materials often interfere with the standard laboratory tests. Therefore this disclosure provides a new method for adequately analyzing the production well effluent by hydrolyzing the sample of effluent containing recovered polymer to release glucose moieties, reacting said moieties with orthotoluidine and determining the concentration of polymer using colorimetric methods. No interference is found from tracers present in the sample.

Tracers susceptible to use in the present invention are those well-known to those skilled in this art such as thiocyanate ion, bromide ion, methanol, or ethanol.

Polymers susceptible to the methods of analysis described herein are those biopolysaccharides having glucose moieties. Representative examples of such polymers are xanthin gums, such as those sold as Kelzan polymers by Kelco Company. Various types of these polymers are available but all can be easily analyzed by the method described herein.

The analytical method generally consists of hydrolyzing the biopolysaccharides for from about ½ to about 24 hours with an acid, such as hydrochloric acid, sulfuric acid, phosphoric acid, or perchloric acid, diluted to about a 20 to 1 ratio, and developing color by reacting the glucose liberated by the hydrolysis with orthotoluidine at temperatures from about 80 to about 105° C for a period of time ranging from 5 to about 20 minutes. The color should be developed with a ratio of sample to reagent of about 1 to about 10, but a ratio of from about 1 to about 6 is preferred. The color of the compound formed, once developed, is measured at from 430–700nm, preferably at 610 nanometers (nm), and a calibration curve is developed by plotting absorbance versus concentration.

The amount of tracer to polymer can range from 1 to 200 parts by weight respectively to 200 to 1 parts by weight respectively. However, normally about equal parts of tracer or mixture of tracer and polymer will be used.

The instant invention is more concretely described with reference to the examples below wherein all parts and percentages are by weight unless otherwise specified. The examples are intended to illustrate the present invention and should not be construed to limit it.

Example 1 describes the method of injecting tracer and polymer into the petroliferous formation, and likewise describes the difference in recovery concentrations. Example 2 describes the method of analysis which is necessary in order to adequately determine polymer content.

EXAMPLE 1

Equal amounts by weight of a tracer material, thiocyanate ion, and a polysaccharide polymer (a Kelzan polymer sold by Kelco Company) is injected into a subterranean petroliferous formation. The injection is continued for several days or weeks. Effluent from a production well is periodically analyzed until traces of the faster eluting polymer are detected. Analysis for both the tracer and the polymer begins at this time and continues until approximately 95% of both have been eluted. The sample for determination of polymers is hydrolyzed in an acid media, reacted with orthotoluidine and the concentration is determined using standard colorimetric methods. A comparison of the rate of elution of the tracer material and the polymer will accurately portray the ratio of larger interstices to small interstices within the formation, and allow an accurate determination of the relative rates of the elution through the formation for various types of waterflood materials.

The produced effluent samples are analyzed for thiocyanate ion tracer by adjusting the pH to about neutral, filtering to remove particulate matter and developing the Iron (III) thiocyanate color using an automated Auto-Analyzer instrument. This device mixes the reagent (iron (III) in about 0.1 N acid) with the sample, passes it through a colorimeter and calculates the concentration by comparing to standards run the same way. Table 1 shows typical calibration data for this system.

TABLE 1

| Calibration Curve for Thyocycnate ion tracer Determination | |
|---|---|
| Absorbance | Tracer Concentration, ppm as $NH_4SCN$ |
| 1.20 | 20.0 |
| 1.90 | 15.0 |
| 0.58 | 10.0 |
| 0.44 | 7.5 |
| 0.29 | 5.0 |
| 0.14 | 2.5 |
| 0.05 | 1.0 |

It should be noted that bromide ion and other chemical tracer concentrations are obtained in a similar way, using different reagents and slightly different sample preparation. The radioactive traces are determined by the appropriate radioactive counting procedure and alcohol tracers are determined by GLC (gas liquid chromotography) techniques.

EXAMPLE 2

The method of the present invention was compared to the resorcinol method of determining polymer content. Various inhibitors of bacterial growth were added at 1,000 parts per million (ppm) concentration, while fresh Kelzan polymer was added at 100 ppm. Aliquots of the solutions were then tested to give direct comparisons of each method. The results are shown in Table 2 and illustrate the acrolein does not mask results to the extent found in the resorcinol method, while giving comparable results when other bacteria inhibitors are used.

Previous methods of analysis determined polymer content using resorcinol, sulfuric acid, and water, followed by using a spectrophotometer of a colorimeter. Interference has been found to be caused by acrolein, oil, salt over a concentration of about 3 percent solids, and sulfonates, while allowing a polymer determination accurate only in a range from about 50 to about 500 parts per million (ppm) concentration by sample weight. The improved method is affected only by acrolein and is efficient from at least about 10 parts per million polymer concentration. When bactericides other than acrolein are used, the method is efficient to about 5 parts per million polymer concentration. When using either acrolein or a substitute bactericide, other interferences are avoided.

The analytical method used based on orthotoluidine does not appear to be critical, although one may be more preferred over another for reasons of convenience. An orthotoluidine method for determining glucose liberated during the hydrolysis can be found described in Analytical Chemistry Volume 45, page 2162, 1973, by H. Y. Yee. A method is also described in *Advances in Automated Analysis,* 1972, Technicon International Congress, Volume 1, MEDIAD, Incorporated, 1973, page 129, authored by Springer, McCune, and Bishop.

A typical laboratory procedure would be divided into two main steps, hydrolysis and colorimetric development. The hydrolysis is accomplished by filtering the water samples using a 0.6 millimicron polyvinylchloride (PVC) millipore filter. Five milliliters of the sample are placed in a screw-capped culture tube, and 0.25 milliliter of concentrated hydrochloric acid is added. The samples are digested in a steam bath overnight at about 95 to 100° C. Calibration standard solutions are prepared in the same manner. the colorimetric determination is made using Technicon Auto-Analyzer equipment or its equivalent by filling the sample wash reservoir with a wash solution, regulating the heating bath to about 90° C, and applying a vacuum to the cooling coil in order to bring the sample to near room temperature before color measurement. A timer is used to measure a sample time of 1 minute and a wash time of 3 minutes. A 50-millimeter cell and colorimeter is used along with 610-nm filters.

Using the method described above, the effect of various inhibitors on Kelzan polymer analysis was determined. The inhibitors checked were Visco 950 and Visco 1150 sold by Nalco Chemical Company, Dowicide B sold by Dow Chemical Company, sodium hydroxide, and acrolein sold by Magna Corp. as Magnacide B. Various concentrations were tested in the absence of polymer, and the effect of the apparent polymer concentration in parts per million was measured. Results are shown in Table 2.

It is apparent from the data given in Table 3 that acrolein at 140 parts per million appears as 1 part per million polymer. This appears to be a straight-line function and is applicable for all concentrations in the parts per million range.

A calibration curve for polymer determination measuring adsorbance versus concentration for Kelzan polymer is shown in Table 4.

It is clear that this method of analysis is sensitive to about 2 parts per million polysaccharide polymer. Because of uncertainty of accuracy due to interferences, values are normally reported only when 5 parts per million polymer is exceeded. The method was tested for interferences due to bactericides and inhibitors that have been added to normal waterfloods. Acrolein alone appears to interfere to a detectable extent, but even so such interference is greatly lessened as compared to prior art methods.

The method described herein is reliable and accurate for the measurement of the glucose moiety obtained from the hydrolysis of the biopolysaccharide polymers. The hydrolysis of the polymer itself can be used as a technique for determining the concentration of the polymer as desired.

TABLE 2

| ORTHOTOLUIDINE AND RESORCINOL METHODS OF ANALYSIS | | | |
|---|---|---|---|
| Inhibitor, | POLYMER CONCENTRATION, ppm | | |
| 1,000 ppm | Added | Resorcinol | Orthotoluidine |
| Visco 950 | 100 | 105 | 102 |
| Dowicide B | 100 | 105 | 96 |
| Sodium Hydroxide | 100 | 105 | 103 |
| Acrolein | 100 | 174 | 110 |
| Blank | 100 | 100 | 100 |

TABLE 3

| INHIBITOR EFFECT | | |
|---|---|---|
| Inhibitor | Inhibitor Concentration, ppm | Apparent Polymer, ppm |
| Visco 950 | 1,000 | 0 |
| Visco 1150 | 1,000 | 0 |
| Dowicide B | 1,000 | 0 |
| Sodium Hydroxide | pH 12 | 0 |
| Acrolein | 1,250 | 8.6 |

TABLE 4

| CALIBRATION CURVE FOR POLYMER DETERMINATION | |
|---|---|
| Absorbance | Polymer Concentration, ppm |
| 0.022 | 10 |
| 0.023 | 10 |
| 0.057 | 25 |
| 0.058 | 25 |
| 0.115 | 50 |
| 0.116 | 50 |
| 0.169 | 75 |
| 0.172 | 75 |
| 0.246 | 100 |
| 0.240 | 100 |

No interference of tracers is noted when using the method of the present invention is used for polymer determination, and the same is true when of the polymer when tracer concentration is determined. Relative flow rates for known core samples are easily determined, accurate information regarding flow characteristics of formations can be obtained when comparisons to known standards are made.

While certain embodiments and details have been shown for the purpose of illustrating this invention, it will be apparent to those skilled in this art that various changes and modifications may be made herein without departing from the spirit or the scope of the invention.

We claim:

1. A method for determining the flow characteristics of subterranean petroliferous formations by simultaneously injecting a tracer and a polysaccharide polymer having glucose moieties into said formations, recovering said tracer and polysaccharide from production well effluent at timed intervals and determining flow characteristics by the rate differential observed between recovered tracer and polysaccharedi polymer, wherein the concentration of polysaccharide polymer is observed by;
   a. hydrolyzing the polymer to liberate glucose,
   b. reacting the liberated glucose with orthotoluidine, and
   c. determining the polymer concentration using colorimetric determination.

2. A method as described in claim 1 wherein the hydrolysis is carried out for 178 to 24 hours in the presence of an acid selected from the group consisting of hydrochloric, sulfuric, phosphoric, and perchloric.

3. A method as described in claim 1 wherein the glucose is reacted with orthotoluidine at about 90° C.

4. A method as described in claim 3 wherein the reaction is carried out for from about 8 to about 15 minutes and the weight ratio of sample to the reagent is from about 1 to about 10, respectively.

5. A method as described in claim 1 wherein the colorimetric determination is measured at 430–700 nm.

6. A method as described in claim 1 wherein the tracer material is selected from the group consisting of thiocyanate ion, bromide ion, methanol, ethanol or radioactive materials.

7. A method as described in claim 1 wherein the ratio of polysaccharide to tracer is from about 1:200 parts by weight to about 200:1 parts by weight respectively.

UNITED STATES PATENT OFFICE
CERTIFICATE OF CORRECTION

PATENT NO. : 4,058,366
DATED : November 15, 1977
INVENTOR(S) : Dale K. Cabbiness It is certified that error appears in the above-identified patent and that said Letters Patent are hereby corrected as shown below:

Column 2, line 39, "small" should be --smaller--.

Column 3, line 30, "about" before 5 was left out.

Column 4, line 12, "N" not underlined.

Column 4, line 45, "the" should be --that--.

Column 4, line 51, "of" should be --or--.

Column 6, line 51, "178" should be --1/2--.

Signed and Sealed this

Fourteenth Day of March 1978

[SEAL]

Attest:

RUTH C. MASON
Attesting Officer

LUTRELLE F. PARKER
Acting Commissioner of Patents and Trademarks